United States Patent [19]

Weinstock et al.

[11] 4,131,618

[45] Dec. 26, 1978

[54] PREPARATION OF SALICYLIC ACID AND DERIVATIVES

[75] Inventors: Leonard M. Weinstock, Bellemead; Arthur S. Wildman, Martinsville; Dennis M. Mulvey, Milford, all of N.J.

[73] Assignee: Merck & Co., Inc., Rahway, N.J.

[21] Appl. No.: 865,563

[22] Filed: Dec. 29, 1977

[51] Int. Cl.² ............................................. C07C 65/14
[52] U.S. Cl. .................................. 562/469; 562/474; 562/477; 562/475; 562/468
[58] Field of Search ......................... 260/520 A, 520 E

[56] References Cited

U.S. PATENT DOCUMENTS

| 3,714,226 | 1/1973 | Rugle | 260/473 S |
| 3,992,459 | 11/1976 | Utng et al. | 260/649 F |

OTHER PUBLICATIONS

H. E. Zaugg, J. Org. Chem., vol. 41, No. 21, 3419-3421 (1976).

*Primary Examiner*—Paul J. Killos
*Attorney, Agent, or Firm*—Raymond M. Speer; Mario A. Monaco

[57] ABSTRACT

The invention relates to an improved method of preparing salicylic acid and derivatives from phenyl esters which comprises the step of fusing acetoxyphenyl, or derivative suitable for preparing the desired salicylic acid derivative, with $M_2CO_3$ where M is potassium or sodium in the presence of carbon dioxide, at a temperature of from 150° to 250° C., and at a pressure of from atmospheric to 500 p.s.i.g.

12 Claims, No Drawings

PREPARATION OF SALICYLIC ACID AND DERIVATIVES

BACKGROUND OF THE INVENTION

1. Field of the Invention

The present invention is concerned with an improved method of preparing salicylic acid and derivatives thereof employing as a starting material acetoxyphenyl, or a derivative thereof suitable for preparing the desired derivative of salicylic acid.

More particularly, the present invention is concerned with preparation of 2',4'-difluoro-4-hydroxy-[1,1'-biphenyl]-3-carboxylic acid, an important anti-inflammatory and analgesic therapeutic agent.

2. Description of the Prior Art

Industrial preparation of salicylic acid has long been carried out by the Kolbe-Schmitt reaction in which sodium phenoxide and carbon dioxide are heated at 120°–140° C. under pressure. A small amount of the p-derivative is formed at the same time, and if the temperature rises above 140° C., the p-isomer is the main product. The Kolbe-Schmitt reaction, in turn, is one step in a potentially important process of preparing 2',4'-difluoro-4-hydroxy-[1,1'-biphenyl]-3-carboxylic acid, referred to above. See U.S. Pat. No. 3,992,459. In that process, the intermediate which is converted to the starting material for the Kolbe-Schmitt reaction is a phenyl acetate ester. Accordingly, that process is characterized by the disadvantages of involving cumbersome ester saponification and requiring sodium salt isolation, with attendant drying problems. Thus, the method of the present invention constitutes an improvement of that potentially important process whereby the described disadvantages are avoided and one step is removed from the overall process.

It is known to carry out selective cleavage of aryl esters with anhydrous alkali carbonates. See H. E. Zaugg, J. Org. Chem., Vol. 41, No. 21, (1976) 3419-3421. However, knowledge of this process would not have suggested the novel improvement of the phenyl ester to salicylic acid process accomplished by the method of the present invention, with the unexpected result of achieving a facile, one-step preparation characterized by high yields.

SUMMARY OF THE INVENTION

The present invention relates to an improved method of preparing salicylic acid and derivatives thereof having the following formula:

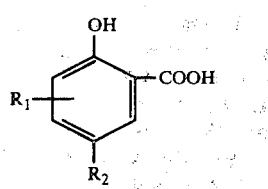

wherein:
$R_1$ is selected from the group consisting of hydrogen, $C_{1-4}$ alkyl, $C_{1-4}$ alkoxy, benzyl, $C_{1-4}$ alkenyl and halo; and
$R_2$ is hydrogen or

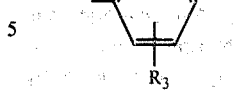

where n is 1 to 5,
X is halogen and
$R_3$ is selected from the group consisting of $C_{1-4}$ alkyl and $C_{1-4}$ alkoxy.

More particularly, the present invention relates to an improved method of preparing compounds of the formula:

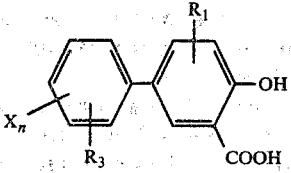

wherein:
$R_1$ and $R_3$ are hydrogen or $C_{1-4}$ alkyl;
n is 2; and
X is chloro or fluoro.

Most particularly, the present invention relates to an improved method of preparing the compound 2',4'-difluoro-4-hydroxy-[1,1'-biphenyl]-3-carboxylic acid, which has the following structural formula:

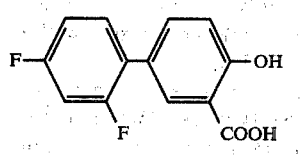

The starting materials for the method of the present invention are compounds of the formula:

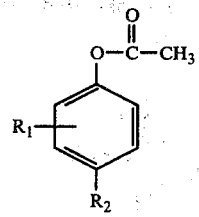

wherein $R_1$ and $R_2$ have the same meanings as above.

Where, in accordance with a preferred aspect of the present invention, the compound prepared is 2'-4'-difluoro-4-hydroxy-[1,1'-biphenyl]-3-carboxylic acid, the starting material is 2',4'-difluoro-4-acetoxy-1,1'-biphenyl.

The acetoxyphenyl starting materials for the method of the present invention may be prepared in accordance with procedures described in U.S. Pat. No. 3,992,459, referred to above.

The improved preparation method of the present invention is a one step method in which the starting material is fused with a substantially anhydrous compound of formula: $M_2CO_3$, where M is potassium or sodium. Potassium carbonate is preferred. The carbonate material may be employed in amounts such that 1 to 5 moles of carbonate for every mole of starting material are present in the reaction mixture. Preferably, the molar ratio is about 2:1.

Since water interferes with the overall reaction, it is necessary that the method of the present invention be carried out under substantially anhydrous conditions, although a trace of water can be tolerated.

The method of the present invention is carried out in the presence of carbon dioxide, the introduction of which is preferably accomplished by pressurizing the reaction vessel, which is sealed, with carbon dioxide. Pressurization is not, however, required. Where pressure is employed, pressures of from 10 to 500 p.s.i.g. are useful, while pressures of from 50 to 400 p.s.i.g. are preferred. Thus, the total pressure range if from atmospheric to 500 p.s.i.g. The use of pressure assures that the carbon dioxide will again access to the other reactants, which are in solid form and have been fused. The volume of the pressurized reaction vessel should be adequate to assure that there will be a considerable excess of carbon dioxide when the vessel is pressurized with carbon dioxide to within the range of pressures described above.

Introduction of the carbon dioxide may also, optionally, be by employing an excess of the carbonate material, whereby, upon a partial decomposition thereof, carbon dioxide gas is released to the reaction environment.

The temperature at which the method of the present invention is carried out should be in the range of from 150° to 250° C., preferably in the range of from 150° to 200° C. Most preferably, the temperature will be in the range of from 175° to 195° C.

The method of the present invention possesses the advantages of being easily carried out, and of resulting in high yields of final product of 90% and higher.

It is considered that the reactions taking place during the method of the present invention are a combination of a concerted process and a stepwise process, with the stepwise route predominating. The concerted reaction route may be illustrated as follows:

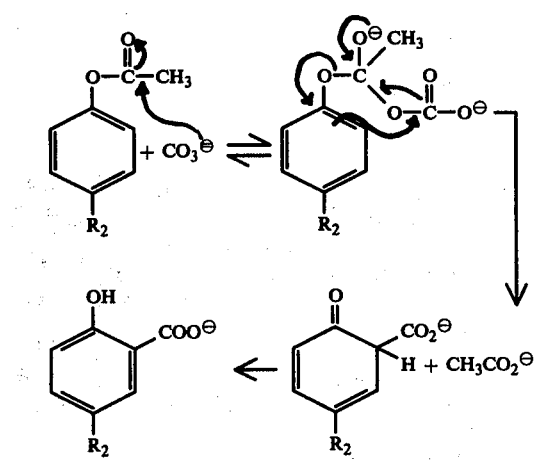

The stepwise reaction route may be illustrated as follows:

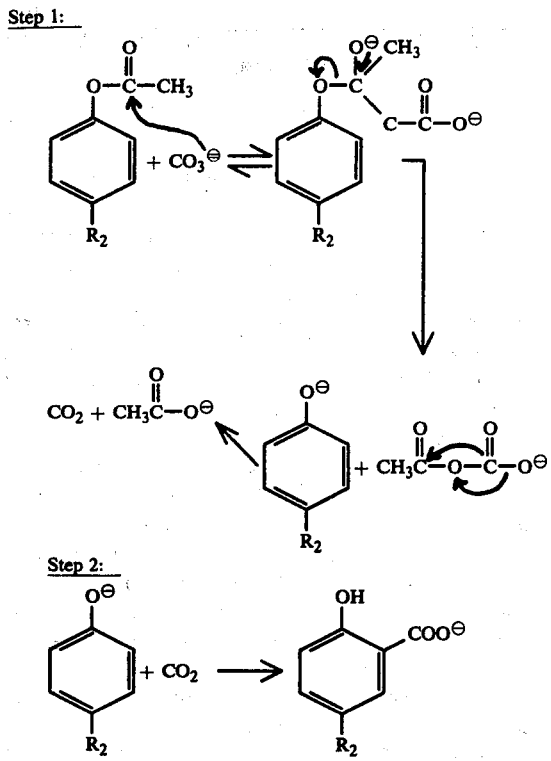

The following example will serve to illustrate the manner in which the method of the present invention may be carried out.

EXAMPLE

A mixture of 12.4 g (0.05 m) of 2,4-difluoro-4'-acetoxybiphenyl plus 13.8 g (0.1 m) freshly ground and vacuum dried (70° C., 12 hr.,50 mm. Hg) potassium carbonate was charged to a sealed bomb and pressurized with carbon dioxide to 400 p.s.i.g. The reaction mixture was then heated to 190° C. and maintained there for six hours with agitation. After cooling, a pressure of 380 pounds was observed. The bomb was vented and the solid mass broken up with a spatula and rinsed from the bomb with about 200 ml. 2.5 N hydrochloric acid. This mixture was aged with stirring for 30 minutes at 70°–75° C. The precipitate was then isolated, washed with about 75 ml. water and was dried at 70° C. in vacuo for 16 hours. In this fashion, 13.33 g. (106%) of crude 2',4'-difluoro-4-hydroxy-[1,1'-biphenyl]-3-carboxylic acid was obtained. This crude product was dissolved in 150 ml. water containing 8.0 g. 50% sodium hydroxide solution at 90° C. Then 0.25 g. disodium salt of ethylenediaminetetracetic acid plus 1 g. charcoal (Merck ACM) were introduced and the solution aged 20 minutes at 90°–95° C. The solution was filtered hot and the cake washed with 4 × 25 ml. of hot water (75° C.). Then 130 ml. of 2-propanol were added and the solution heated to 80° C. To this well-stirred solution was added dropwise 5 ml. of concentrated sulfuric acid. The reaction mixture was allowed to cool to 78° C. and was seeded with 2',4'-difluoro-4-hydroxy-[1,1'-biphenyl]-3-carboxylic acid. After aging 1 hr. at 75°–80° C., the solution was allowed to slowly cool to 20° C. (about 1½ hr.). The colorless precipitate was isolated and washed with 100 ml. of 2:1 water: 2-propanol, followed with 75 ml. of water. After drying at 70° C. for 16 hrs. in vacuo 50 mm. Hg. 11.25 g. (90%) of colorless 2',4'-difluoro-4-hydroxy-[1,1'-biphenyl]-3-carboxylic acid was obtained. A second crop was obtained by chilling the mother liquors overnight; the yield was 0.30 g. (2.4%), M.P., 165–190° C.

The salicylic acid and salicylic acid derivatives prepared by the method of the present invention are valuable compounds which are useful in a variety of important areas. Salicylic acid, for example, is useful as an antiseptic agent, and as an intermediate in the manufacture of dye-stuffs. In particular, 2',4'-difluoro-4-hydroxy-[1,1'-biphenyl]-3-carboxylic acid and derivatives thereof are valuable anti-inflammatory and analgesic agents for therapeutic use. See U.S. Pat. No. 3,714,226.

What is claimed is:

1. A method of preparing compounds of the formula:

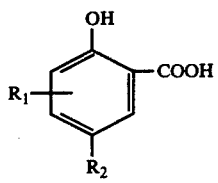

wherein:
$R_1$ is selected from the group consisting of hydrogen, $C_{1-4}$ alkyl, $C_{1-4}$ alkoxy, benzyl, $C_{1-4}$ alkenyl and halo; and
$R_2$ is hydrogen or

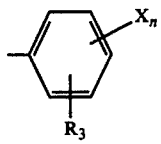

where n is 1 to 5,
X is halogen, and
$R_3$ is selected from the group consisting of $C_{1-4}$ alkyl and $C_{1-4}$ alkoxy;
comprising the step of fusing a starting material selected from compounds of the formula:

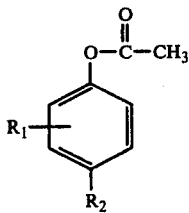

wherein $R_1$ and $R_2$ are as defined above; with a substantially anhydrous compound of the formula:

$M_2CO_3$ where M is potassium or sodium; under substantially anhydrous conditions and in the presence of carbon dioxide, at a pressure of from atmospheric to 500 p.s.i.g., and at a temperature of from 150° to 250° C.

2. The method of claim 1 wherein M is potassium.

3. The method of claim 1 wherein the pressure is from 50 to 400 p.s.i.g.

4. The method of claim 1 wherein the temperature is from 150° to 200° C.

5. A method of preparing compounds of the formula:

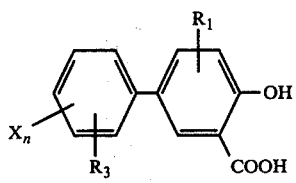

wherein:
$R_1$ and $R_3$ are hydrogen or $C_{1-4}$ alkyl,
n is 2, and
X is chloro or fluoro; comprising the step of fusing a starting material selected from compounds of the formula:

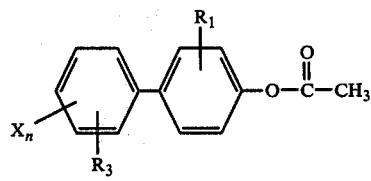

wherein $R_1$, $R_3$, n, and X are as defined above; with a substantially anhydrous compound of the formula:

$M_2CO_3$ where M is potassium or sodium; under substantially anhydrous conditions and in the presence of carbon dioxide, at a pressure of from atmospheric to 500 p.s.i.g., and at a temperature of from 150° to 250° C.

6. The method of claim 5 wherein M is potassium.

7. The method of claim 5 wherein the pressure is from 50 to 400 p.si.g.

8. The method of claim 5 wherein the temperature is from 150° to 250° C.

9. A method of preparing the compound 2', 4'-difluoro-4-hydroxy-[1,1'-biphenyl]-3-carboxylic acid; comprising the step of fusing the starting material 2', 4'-difluoro-4-acetoxy-1,1'-biphenyl with a substantially anhydrous compound of the formula: $M_2CO_3$, where M is potassium or sodium; under substantially anhydrous conditions and in the presence of carbon dioxide, at a pressure of from atmospheric to 500 p.s.i.g., and at a temperature of from 150° to 250° C.

10. The method of claim 9 wherein M is potassium.

11. The method of claim 9 wherein the pressure is from 50 to 400 p.s.i.g.

12. The method of claim 9 wherein the temperature is from 150° to 250° C.

* * * * *